United States Patent [19]

Farzin-Nia

[11] Patent Number: 5,419,047

[45] Date of Patent: May 30, 1995

[54] STAINLESS STEEL PLIER-TYPE CUTTERS

[75] Inventor: Farrokh Farzin-Nia, Inglewood, Calif.

[73] Assignee: Ormco Corporation, Glendora, Calif.

[21] Appl. No.: 62,960

[22] Filed: May 14, 1993

[51] Int. Cl.$^6$ .............................................. B26B 17/00
[52] U.S. Cl. .................................... 30/254; 30/350; 76/119
[58] Field of Search ............... 30/244, 194, 112, 186, 30/208, 254, 350; 140/121; 148/566; 76/119

[56] References Cited

U.S. PATENT DOCUMENTS

| 715,915 | 12/1902 | White | 140/121 |
|---|---|---|---|
| 1,155,882 | 10/1915 | Bryce | 140/121 |
| 1,289,381 | 12/1918 | Brumfield | 140/121 |
| 1,299,102 | 4/1919 | Angle | 140/121 |
| 2,315,326 | 3/1943 | Gmeiner | 30/244 |
| 2,513,778 | 7/1950 | Bailey . | |
| 2,596,770 | 5/1952 | Groven . | |
| 2,620,433 | 12/1952 | Denneen et al. . | |
| 4,492,840 | 1/1985 | Lex . | |
| 4,623,401 | 11/1986 | Derbyshire et al. | 148/566 |
| 5,133,812 | 7/1992 | Kelly et al. | 30/134 |
| 5,184,404 | 2/1993 | Chen | 30/250 |
| 5,301,431 | 4/1994 | Cera | 30/186 |

Primary Examiner—Richard K. Seidel
Attorney, Agent, or Firm—Wood, Herron & Evans

[57] ABSTRACT

Plier-type cutters for cutting metal objects having a pair of plier halves which are each of one piece construction and made of a hardenable stainless steel. Each plier half has a cutting edge hardened to a cutting hardness suitable for cutting the metal object, such as an orthodontic metal appliance, without fracturing during normal use. Each plier half has at least one fracture sensitive portion, excluding its cutting edge, which would be susceptible to fracturing during normal use if hardened to the cutting hardness. Each fracture sensitive portion has a working hardness which is sufficiently lower than the cutting hardness to substantially limit, if not eliminate, the likelihood of fracture during normal use. The present plier-type cutters with differently hardened regions may be obtained by fully hardening each plier half to the desired cutting hardness and then selectively tempering at least the fracture sensitive portions of each while keeping at least the cutting edges relatively cool to prevent significant softening thereof.

9 Claims, 1 Drawing Sheet

STAINLESS STEEL PLIER-TYPE CUTTERS

FIELD OF THE INVENTION

This invention relates to stainless steel plier-type cutting tools, and particularly, to plier-type cutters used to cut orthodontic metal appliances.

BACKGROUND OF THE INVENTION

Plier-type cutters are often used in orthodontics to cut a variety of orthodontic appliances, such as wires, ligatures, facebows, and the like, made of stainless steels, titanium alloys or other orthodontic metals. These orthodontic cutters typically include a pair of plier halves, with each plier half having a handle, a pivot section, and a jaw with a cutting edge. The two plier halves are pivotally connected at their pivot section such that relative movement of the handles will cause relative movement of the jaws. It is desirable for such orthodontic cutters to be made of a material which is corrosion resistant, to have hard cutting edges and for the balance of the cutter to be tough.

Heretofore, one form of these cutters employed cutting edge inserts made of carbide or tool steel which were braised or otherwise secured to the jaw of each plier half, with the balance of each plier half being made of stainless steel, typically 17-4 PH.

In the orthodontic field, as in other medical fields, it is important to maintain clean and sterile instruments. Orthodontic cutters are typically cleaned or sterilized with high temperature steam after every use. The cleaning and sterilizing procedures, and even the orthodontic procedures in which they are used, often subject the cutters to corrosive environments. While carbide and tool steel cutting edge inserts enable the cutter to hold its cutting edge without fracturing, they are not as corrosion resistant as the remaining stainless steel portion of the cutter. Thus, the carbide and tool steel inserts have a tendency to corrode after only limited use, requiring costly rework or replacement. Another disadvantage of such orthodontic cutters is the relatively high cost of manufacturing the cutting edge inserts and mounting those inserts to the jaws of each plier half.

Attempts at making such orthodontic cutters more corrosion resistant have included coating the plier with a corrosion resistant material, such as chrome plating. However, after continued use the protective coating either wears or chips off of at least portions of the cutting edge inserts, exposing the corrodible underlying metal.

SUMMARY OF THE INVENTION

An objective of the present invention is to provide a plier-type cutter for cutting metal objects which is less likely to corrode to the point of requiring re-work or replacement as a result of frequent use and cleaning or sterilization.

Another objective of the present invention is to provide such a corrosion-resistant cutter which exhibits extended cutting edge life.

An additional objective of the present invention is to provide such a corrosion-resistant cutter which is far less likely to fracture during normal use.

A further objective of the present invention is to provide such a corrosion-resistant cutter which is less expensive to manufacture.

These objectives are accomplished by providing a plier-type cutter for cutting metal objects having a pair of plier halves which are each of one-piece construction and made of a hardenable stainless steel. Each of the plier halves includes a handle section and a jaw section. The jaw section includes a cutting edge hardened to a cutting hardness suitable for cutting an object, such as an orthodontic metal appliance, without fracturing during normal use. Each of the plier halves have at least one portion, excluding its cutting edge, which would be susceptible to fracturing during normal use if hardened to the cutting hardness. Each fracture sensitive portion is given a working hardness which is sufficiently lower than the cutting hardness to substantially limit, if not eliminate, the likelihood of fracture during normal use.

The plier halves of such cutters typically include a pivot section located between respective handle and jaw sections. These plier halves are connected together in a pivotal relationship at their pivot section such that relative movement of the handle sections causes relative movement of the jaw sections and therefore the cutting edges.

To help reduce the likelihood of fracture during normal use, the cutter is manufactured using a method which enables the cutting edges to have the cutting hardness and any fracture sensitive portions to have the working hardness. This manufacturing method includes the steps of hardening each of the plier halves to the cutting hardness desired for the cutting edges and then tempering any fracture sensitive portion of each plier half to reduce its hardness to the desired working hardness. These fracture sensitive portions of each plier half are softened until a sufficient degree of toughness is obtained that they are unlikely to fracture during normal use.

In one embodiment of the cutter manufacturing method of this invention, the hardening step includes austenitizing and quenching each of the plier halves in their entirety to the desired cutting hardness. The tempering step for any fracture-prone region may be accomplished by any suitable heating method, including induction heating with one or more induction coils wrapped around at least the fracture sensitive portions of each plier half. Adequate heat sinking of the cutting edges during the tempering step may be accomplished by immersing at least the cutting edge of each plier half into a heat dispersing fluid, such as water, while tempering the fracture-sensitive portions.

The present cutters hold their edge without fracturing during extended normal use and are corrosion resistant. The present cutters are thus suitable as orthodontic cutters for cutting various orthodontic metal appliances, even when subjected to repeated sterilization procedures with high temperature steam. Further, the cost of manufacturing the present plier-type cutter, especially for orthodontic applications, is significantly reduced by virtue of the elimination of any cutting edge insert.

The above and other objectives and advantages of the present invention will become more apparent from the following detailed description of the invention.

DETAILED DESCRIPTION OF THE INVENTION

Figure 1:
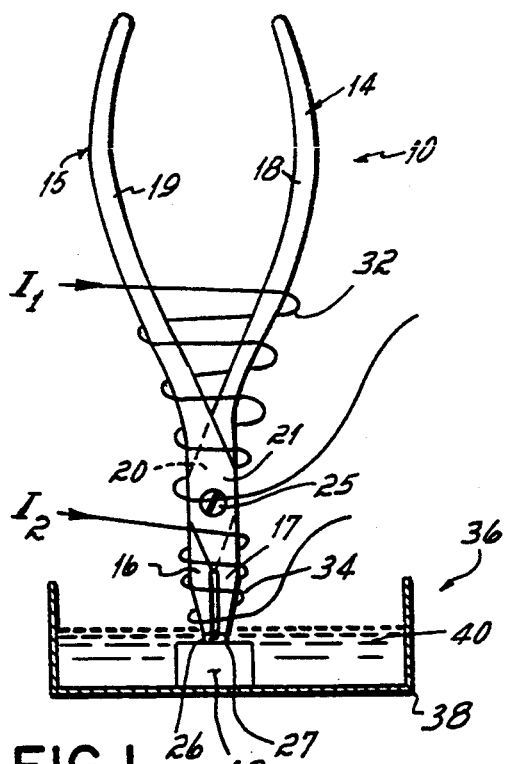
FIG. 1 is a front elevational view, partially diagrammatic, of a distal-end orthodontic archwire cutter being tempered according to the present invention.
Figure 2:
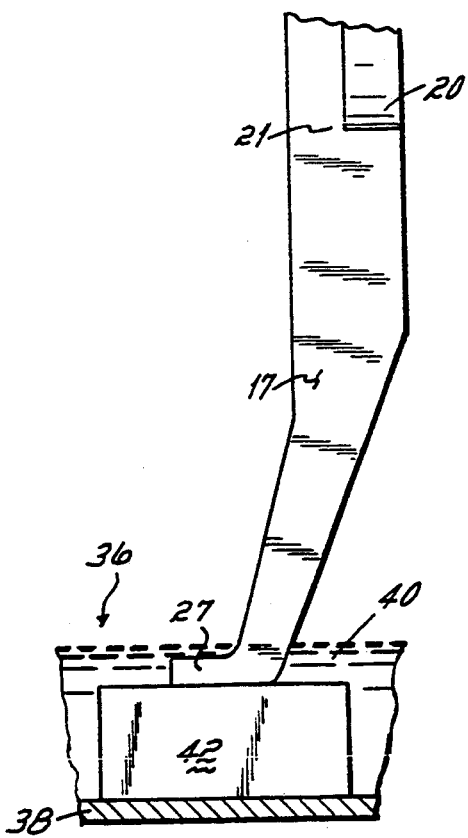
FIG. 2 is an enlarged side elevational view of the cutting jaw sections of the cutter of FIG. 1 with its cutting portions immersed in a heat dispersing fluid during tempering.
Figure 3:
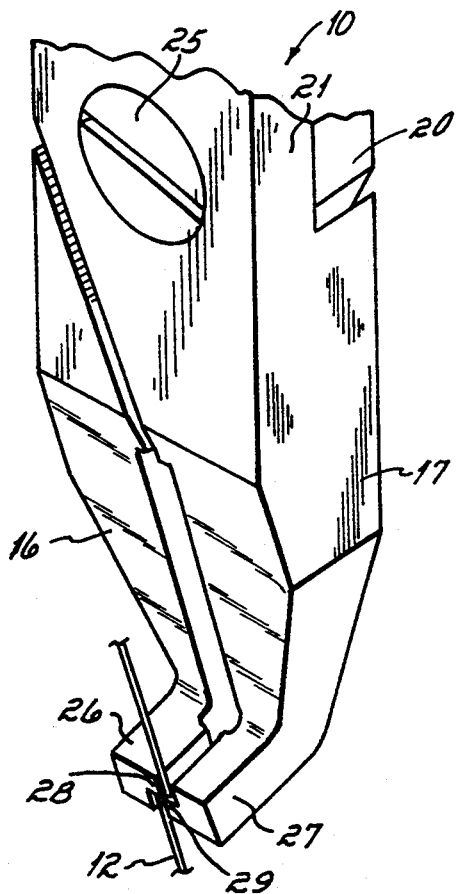
FIG. 3 is an enlarged perspective view of the jaw sections of the cutter of FIG. 1 shown cutting a wire.
Figure 4:
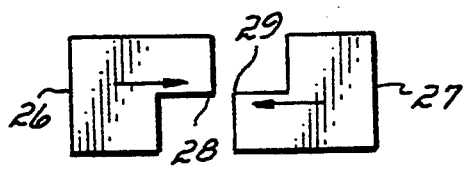
FIG. 4 is an enlarged front view of the cutting edges of the jaw sections of FIG. 3.

The principles of the present invention are applicable to a wide variety of plier-type cutters made of hardenable stainless steel where good corrosion resistance, extended cutting edge life and resistance to fracturing are desirable. Referring to FIGS. 1-4, an exemplary orthodontic distal-end plier-type cutter 10 is shown which is used to sever portions of orthodontic metal appliances, such as archwires 12. The cutter 10 has two plier halves 14 and 15 of one piece construction. Each plier half 14, 15 is made of a hardenable stainless steel, such as ATS-34 manufactured by Hitachi, 440, 420 and 17-4PH. Each plier half 14, 15 includes a jaw section 16, 17 at one end thereof, a handle section 18, 19 at the other end thereof, and a recessed pivot section 20, 21 therebetween, respectively. The recessed pivot sections, 20, 21 are adapted to receive each other in nesting relation and are pivotally connected together, for example by a screw 25, to form a pivot joint. Each jaw section 16, 17 has a respective cutting portion 26, 27. Each cutting portion 26, 27 includes a shear cutting edge 28, 29, respectively. When the recessed pivot sections 20, 21 are connected together by the joint screw 25, the plier halves 14, 15 are able to pivot relative to one another around screw 25. Thus, relative movement of the handle sections 18, 19 causes the jaw sections 16, 17 to open or close and thus the cutting edges 28, 29 to separate or make contact in cutting relation (see FIG. 4).

Holding the cutter 10 by handles 18, 19, an orthodontist can cut the desired archwire or other orthodontic metal appliance (not shown) by spreading the handle sections 18, 19 apart to therein open the jaw sections 16, 17. The archwire 12 is then positioned between the two cutting edges 28, 29 and the handle sections 18, 19 squeezed together. Squeezing the handle sections 18, 19 together closes the jaw sections 16, 17 until the archwire 12 is severed by the cutting edges 28, 29.

During the manufacturing of the cutters 10 according to the present invention, each cutting edge 28, 29 is given a cutting hardness suitable for cutting the orthodontic archwires 12, or other appropriate object, without fracturing during normal use. Each of the plier halves 14, 15 has at least one portion which would be susceptible to fracturing during normal use if it were at a hardness equal to or greater than the cutting hardness of its respective cutting edges 28, 29. For the exemplary cutter 10, the fracture sensitive portions may be the recessed pivot sections 20, 21 and adjoining portions of the handles 18, 19 and jaws 16, 17. This susceptibility to fracturing, when at the cutting hardness, may be due to the fact that the pivot sections 20, 21 are recessed (i.e., there are abrupt changes in the cross section of each plier half 14, 15 in this area). It may also be due to the relatively high stresses generated at the pivot sections 20, 21 during use of the cutter 10. To avoid fracturing of either plier half 14, 15 during normal use, each of these fracture sensitive portions are given a working hardness which is far enough below the cutting hardness of the cutting edges 28, 29 that the cutter 10 is unlikely to fracture at these portions during normal use in cutting objects, like wire 12.

To manufacture cutters 10 according to the principles of the present invention, each plier half 14, 15 is preferably formed into its finished or near finished condition. Each plier half 14, 15, in its entirety, is then hardened to the cutting hardness desired for the particular normal use, such as cutting orthodontic archwires 12. Preferably, the hardening step includes austenitizing and then quenching each of the plier halves to impart the cutting hardness to each plier half. Next, at least the fracture sensitive portions of each plier half is tempered to the working hardness. To ensure that each of these fracture sensitive portions are adequately tempered to reduce the likelihood of fracture during normal use or to reduce manufacturing costs, it may be desirable to temper all of both pivot sections 20, 21 and the adjoining portions of the jaw sections 16, 17 (excluding at least the cutting edge) and the handles 18, 19. The tempering step may be accomplished by any satisfactory heating method.

Preferably, tempering is accomplished by induction heating with at least one and preferable two induction coils 32, 34. Techniques for induction heating with induction coils are well known and therefore will not be discussed in detail herein. In summary, for optimum efficiency, each coil 32, 34 should be placed as close as possible to the surface being heated without making contact between the coil and the surface. Previously, such coils 32, 34 have been used to harden a portion of a steel object. In the present method, the induction coils 32, 34 are being used to temper or reduce the hardness of previously hardened portions of the cutter 10. Therefore, it may not be necessary to maintain tight tolerances with respect to the closeness of coils 32, 34 in order to effectively temper the fracture sensitive portions of cutter 10.

While the tempering step may be conducted on each plier half individually, it has been found cost effective to assemble each plier half 14, 15 into cutter 10 and then encircle the lower portion of both handles 18, 19 and the pivot sections 20, 21 with coil 32. The jaw section 16, 17, excluding at least the cutting edges 28, 29 and preferably the cutting portions 26, 27, are encircled by coil 34. A current $I_1$ is passed through coil 32 and a second current $I_2$ is passed through coil 34 to produce induction heating therewith. Currents $I_1$ and $I_2$ may be different or the same depending upon the heating requirements during the tempering step. In addition, it may be desirable for the coils 32, 34 to be positioned and utilized at the same time or, alternatively, in separate tempering steps.

While the fracture sensitive portions of cutter 10 are being tempered to the working hardness desired, at least the cutting edges 28, 29 and preferably the cutting portions 26, 27, are kept relatively cool to maintain their cutting hardness. A heat sink 36 may be used for this purpose. Heat sink 36 may include a reservoir 38 containing a heat dispersing fluid 40, preferably water. The cutting portions 26, 27 of the cutter 10 are immersed in the fluid 40 during the tempering step. A block 42 may be placed inside of reservoir 38 and positioned underneath cutting portions 26, 27 to help ensure consistency during mass production of cutters 10. Thus by heat sinking cutting portions 26, 27 in this manner, or in any other similar manner, a pair of plier-type cutters 10 can be produced which is corrosion resistant due to the use of a hardenable stainless steel, has an extended cutting life due to the hardened cutting edges 28, 29 and is less likely to fracture because the hardness of those portions susceptible to fracturing have been reduced a sufficient amount.

In an exemplary manufacturing process, a number of orthodontic distal-end plier-type cutters 10 were made from a stainless steel, ATS-34, manufactured by Hitachi Metals America Ltd., Long Beach, Calif. This stainless steel has a general composition by weight percent of:

| | |
|---|---|
| Carbon | about 1.05% |
| Silicon | about .02% |
| Manganese | about .04% |
| Chromium | about 14.00% |
| Molybdenum | about 4.00% |
| Iron | balance. |

Each plier half 14, 15 was formed from this stainless steel material into its finished shape, except for putting a final edge on cutting edges 28, 29. Next, each plier half 14, 15 was heat treated in a vacuum at a temperature of about 1925° C. for a period of about 30 minutes. Next, the plier halves 14, 15 were quenched in a gas of $N_2$ to a cutting hardness of about RC 61 to about 63. The hardened plier halves 14, 15 were then assembled together, such as previously described with screw 25. The now assembled cutters 10 were then tempered in the same manner as previously described using the two induction coils 32, 34. Induction heating was accomplished two different times at the two different regions of the cutters 10 rather than simultaneously. The fully hardened cutters 10 were tempered at a temperature of approximately 500° C. around the pivot sections 20, 21, as previously described, to reduce the hardness of load bearing areas to within the range of about RC 42 to about 58. Two to three percent of the cutters 10 having a working hardness above about RC 55 were found to fracture during normal use. Those cutters 10 which had their fracture-sensitive regions tempered to a working hardness of about RC 55 or less did not fracture during extended normal use. During tempering, the cutting edges 28, 29 and the cutting portions 26, 27 were immersed in a container 38 of water 40, in the manner previously described, in order to rapidly draw away any heat from the tempering step transferred to the cutting portions 26, 27. This is done in order to avoid any overheating and thereby any significant softening of the cutting edges 28, 29. At the conclusion of tempering, the hardness of the cutting edges 28, 29 and cutting portions 26, 27 remained unchanged in the range of about RC 61–63.

Orthodontic cutters 10 are intended to be reused numerous times and subjected to standard orthodontic sterilization procedures subsequent to each use. Therefore, to function properly in this environment, the cutter 10 should not only hold its cutting edge without fracturing, it should also resist the corrosive effects of such repeated and extended use in subsequent sterilization. Unlike prior orthodontic cutters (not shown) which use corrodible cutting edge inserts in its cutting jaws, the plier halves 14, 15 of the present cutter 10 are made entirely of stainless steel and are fully corrosion resistant. At the same time, because it has been selectively heat treated as described above, the present cutter 10 can have an edge which is sufficiently hard to ensure an extended cutting life while at the same time fracture sensitive portions are toughened to be less susceptible to fracturing during normal use. In addition, cutters 10 according to the principles of the present invention can be manufactured less expensively than prior orthodontic cutters utilizing cutting edge inserts because of their one piece construction.

While only one embodiment of the cutters and cutter manufacturing method of the present invention has been described in detail, the present invention is not to be limited solely to these embodiments. A person skilled in the art will readily appreciate changes and modifications which may be made without departing from the spirit of the present invention. Therefore, this invention is not intended to be limited except by the scope of the following claims.

What is claimed is:

1. A plier-type cutter resistant to corrosion from wet steam sterilization comprising:

a pair of plier halves made of a hardenable stainless steel, each of said plier halves being of one piece construction and including a stainless steel handle section and a stainless steel insert-free jaw section, said jaw section including a stainless steel cutting edge having a cutting hardness capable of cutting a metal object without fracturing during use, at least one of said plier halves having at least one fracture-sensitive portion, other than said cutting edge, said at least one fracture-sensitive portion having a working hardness significantly lower than said cutting hardness, and said at least one fracture-sensitive portion exhibiting enhanced toughness sufficient to render it significantly less prone to fracturing during use when at said lower working hardness than would otherwise result were said at least one fracture-sensitive portion at said higher cutting hardness; and connecting means for connecting said pair of plier halves together such that relative movement of said handle sections causes relative movement of said cutting edges for cutting objects.

2. The cutter of claim 1, each of said cutting edges having a hardness of at least about RC 61.

3. The cutter of claim 2, each of said cutting edges having a hardness within the range of about RC 61 to about RC 63.

4. The cutter of claim 1, said working hardness being at least about RC 42.

5. The cutter of claim 4, said working hardness being within the range of about RC 42 to about RC 58.

6. The cutter of claim 1, each of said jaw sections having a geometric configuration suitable for cutting portions of orthodontic metal appliances.

7. The cutter of claim 1, each of said plier halves including a pivot section, and said at least one portion including at least part of said pivot section.

8. The cutter of claim 7, at least one of said pivot sections being recessed to receive the other of said pivot sections.

9. The cutter of claim 1, each of said plier halves being made of a hardenable stainless steel from the group consisting of ATS-34, 440, 420 and 17-4PH.

* * * * *